(12) United States Patent
West et al.

(10) Patent No.: US 8,321,366 B2
(45) Date of Patent: *Nov. 27, 2012

(54) SYSTEMS AND METHODS FOR AUTOMATICALLY RESOLVING INTERACTION BETWEEN PROGRAMMABLE PARAMETERS

(75) Inventors: Jeff West, Bellevue, WA (US); Jay A. Tzucker, Kirkland, WA (US); Mahesh Maddali, Mahtomedi, MN (US); James Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/178,085

(22) Filed: Jul. 7, 2011

(65) Prior Publication Data

US 2011/0264616 A1  Oct. 27, 2011

Related U.S. Application Data

(63) Continuation of application No. 12/566,212, filed on Sep. 24, 2009, now Pat. No. 7,979,378, which is a continuation of application No. 11/380,570, filed on Apr. 27, 2006, now Pat. No. 7,613,672.

(51) Int. Cl.
    *G06N 5/02* (2006.01)
    *A61B 5/00* (2006.01)
    *A61N 1/00* (2006.01)

(52) U.S. Cl. .......... 706/48; 706/924; 600/333; 607/119; 128/924

(58) Field of Classification Search .............. 706/45, 706/48, 924; 128/924; 439/909; 600/333; 607/9, 119, 30–32

See application file for complete search history.

(56) References Cited

U.S. PATENT DOCUMENTS

| | | | |
|---|---|---|---|
| 4,006,737 A | 2/1977 | Cherry | |
| 4,090,505 A | 5/1978 | Mortara | |
| 4,166,470 A | 9/1979 | Neumann | |
| 4,172,459 A | 10/1979 | Hepp | |
| 4,187,854 A | 2/1980 | Hepp et al. | |
| 4,197,850 A | 4/1980 | Schulman et al. | |
| 4,208,008 A | 6/1980 | Smith | |

(Continued)

FOREIGN PATENT DOCUMENTS

EP  0565084  10/1993

(Continued)

OTHER PUBLICATIONS

"U.S. Appl. No. 11/380,570, Non-Final Office Action mailed Dec. 22, 2008", 14 pgs.

(Continued)

*Primary Examiner* — Jeffrey A Gaffin
*Assistant Examiner* — Benjamin Buss
(74) *Attorney, Agent, or Firm* — Schwegman Lundberg & Woessner, P.A.

(57) ABSTRACT

This document discusses, among other things, a system capable of resolving interactions between programmable parameters for operation of a medical device. Programming these devices is a difficult task when many parameters are involved. The disclosed systems and methods attempt to reduce and minimize constraint violations between interdependent parameters using an initial set of parameter values supplied by user (typically a physician) input or calculated automatically, and constraint violations describing invalid parameter values. If possible, a set of parameter values with less egregious constraint violations is generated and may be displayed to the user. A user is prompted to accept the set of parameter values and program the medical device.

19 Claims, 14 Drawing Sheets

U.S. PATENT DOCUMENTS

| | | |
|---|---|---|
| 4,232,679 A | 11/1980 | Schulman |
| 4,236,524 A | 12/1980 | Powell et al. |
| 4,316,249 A | 2/1982 | Gallant et al. |
| 4,323,074 A | 4/1982 | Nelms |
| 4,336,810 A | 6/1982 | Anderson et al. |
| 4,407,288 A | 10/1983 | Langer et al. |
| 4,432,360 A | 2/1984 | Mumford et al. |
| 4,509,530 A | 4/1985 | Curtis et al. |
| 4,529,401 A | 7/1985 | Leslie et al. |
| 4,549,552 A | 10/1985 | Groch et al. |
| 4,680,708 A | 7/1987 | Ambos et al. |
| 4,726,380 A | 2/1988 | Vollmann et al. |
| 4,809,697 A | 3/1989 | Causey, III et al. |
| 4,825,869 A | 5/1989 | Sasmor et al. |
| 4,947,857 A | 8/1990 | Albert et al. |
| 4,958,632 A | 9/1990 | Duggan |
| 4,969,460 A | 11/1990 | Callaghan et al. |
| 4,974,598 A | 12/1990 | John |
| 4,979,506 A | 12/1990 | Silvian |
| 4,989,610 A | 2/1991 | Patton et al. |
| 5,000,189 A | 3/1991 | Throne et al. |
| 5,012,814 A | 5/1991 | Mills et al. |
| 5,027,824 A | 7/1991 | Dougherty et al. |
| 5,046,504 A | 9/1991 | Albert et al. |
| 5,047,930 A | 9/1991 | Martens et al. |
| 5,050,612 A | 9/1991 | Matsumura |
| 5,052,395 A | 10/1991 | Burton et al. |
| 5,107,850 A | 4/1992 | Olive |
| 5,113,869 A | 5/1992 | Nappholz et al. |
| 5,159,926 A | 11/1992 | Ljungstroem |
| 5,184,614 A | 2/1993 | Collins et al. |
| 5,193,550 A | 3/1993 | Duffin |
| 5,215,083 A | 6/1993 | Drane et al. |
| 5,224,475 A | 7/1993 | Berg et al. |
| 5,267,346 A | 11/1993 | Maruyama et al. |
| 5,273,049 A | 12/1993 | Steinhaus et al. |
| 5,292,341 A | 3/1994 | Snell |
| 5,299,118 A | 3/1994 | Martens et al. |
| 5,309,919 A | 5/1994 | Snell et al. |
| 5,311,873 A | 5/1994 | Savard et al. |
| 5,311,874 A | 5/1994 | Baumann et al. |
| 5,312,448 A | 5/1994 | Hognelid et al. |
| 5,315,512 A | 5/1994 | Roth |
| 5,341,811 A | 8/1994 | Cano |
| 5,342,402 A | 8/1994 | Olson et al. |
| 5,344,430 A | 9/1994 | Berg et al. |
| 5,360,437 A | 11/1994 | Thompson |
| 5,371,851 A | 12/1994 | Pieper et al. |
| 5,379,776 A | 1/1995 | Murphy et al. |
| 5,404,877 A | 4/1995 | Nolan et al. |
| 5,411,528 A | 5/1995 | Miller et al. |
| 5,421,830 A | 6/1995 | Epstein et al. |
| 5,423,871 A | 6/1995 | Hoegnelid et al. |
| 5,431,691 A | 7/1995 | Snell et al. |
| 5,433,198 A | 7/1995 | Desai |
| 5,447,164 A | 9/1995 | Shaya et al. |
| 5,458,623 A | 10/1995 | Lu et al. |
| 5,464,433 A | 11/1995 | White et al. |
| 5,480,422 A | 1/1996 | Ben-Haim |
| 5,487,754 A | 1/1996 | Snell et al. |
| 5,487,755 A | 1/1996 | Snell et al. |
| 5,496,351 A | 3/1996 | Plicchi et al. |
| 5,507,786 A | 4/1996 | Morgan et al. |
| 5,513,645 A | 5/1996 | Jacobson et al. |
| 5,523,942 A | 6/1996 | Tyler et al. |
| 5,535,753 A | 7/1996 | Petrucelli et al. |
| 5,549,646 A | 8/1996 | Katz et al. |
| 5,549,654 A | 8/1996 | Powell |
| 5,555,888 A | 9/1996 | Brewer et al. |
| 5,578,063 A | 11/1996 | Bocek et al. |
| 5,584,298 A | 12/1996 | Kabal |
| 5,603,331 A | 2/1997 | Heemels et al. |
| 5,607,460 A | 3/1997 | Kroll et al. |
| 5,609,612 A | 3/1997 | Plicchi et al. |
| 5,613,495 A | 3/1997 | Mills et al. |
| 5,620,471 A | 4/1997 | Duncan |
| 5,620,472 A | 4/1997 | Rahbari |
| 5,620,474 A | 4/1997 | Koppman |
| 5,626,620 A | 5/1997 | Kieval et al. |
| 5,626,623 A | 5/1997 | Kieval et al. |
| 5,628,321 A | 5/1997 | Scheib et al. |
| 5,636,328 A | 6/1997 | Kautz et al. |
| 5,643,255 A | 7/1997 | Organ |
| 5,647,369 A | 7/1997 | Petrucelli et al. |
| 5,674,249 A | 10/1997 | De Coriolis et al. |
| 5,682,489 A | 10/1997 | Harrow et al. |
| 5,683,431 A | 11/1997 | Wang |
| 5,687,737 A | 11/1997 | Branham et al. |
| 5,693,075 A | 12/1997 | Plicchi et al. |
| 5,697,959 A | 12/1997 | Poore |
| 5,713,366 A | 2/1998 | Armstrong et al. |
| 5,713,937 A | 2/1998 | Nappholz et al. |
| 5,716,382 A | 2/1998 | Snell |
| 5,716,383 A | 2/1998 | Kieval et al. |
| 5,716,384 A | 2/1998 | Snell |
| 5,722,999 A | 3/1998 | Snell |
| 5,724,985 A | 3/1998 | Snell et al. |
| 5,725,559 A | 3/1998 | Alt et al. |
| 5,743,268 A | 4/1998 | Kabal |
| 5,749,900 A | 5/1998 | Schroeppel et al. |
| 5,749,906 A | 5/1998 | Kieval et al. |
| 5,749,907 A | 5/1998 | Mann |
| 5,755,736 A | 5/1998 | Gillberg et al. |
| 5,755,742 A | 5/1998 | Schuelke et al. |
| 5,759,199 A | 6/1998 | Snell et al. |
| 5,772,604 A | 6/1998 | Langberg et al. |
| 5,785,660 A | 7/1998 | van Lake et al. |
| 5,788,640 A | 8/1998 | Peters |
| 5,792,203 A | 8/1998 | Schroeppel |
| 5,792,204 A | 8/1998 | Snell |
| 5,803,084 A | 9/1998 | Olson |
| 5,810,740 A | 9/1998 | Paisner |
| 5,814,088 A | 9/1998 | Paul et al. |
| 5,817,137 A | 10/1998 | Kaemmerer |
| 5,833,623 A | 11/1998 | Mann et al. |
| 5,836,989 A | 11/1998 | Shelton |
| 5,839,989 A | 11/1998 | Saito et al. |
| 5,843,138 A | 12/1998 | Evers et al. |
| 5,876,353 A | 3/1999 | Riff |
| 5,891,043 A | 4/1999 | Ericksen et al. |
| 5,891,178 A | 4/1999 | Mann et al. |
| 5,891,179 A | 4/1999 | Er et al. |
| 5,897,577 A | 4/1999 | Cinbis et al. |
| 5,908,392 A | 6/1999 | Wilson et al. |
| 5,924,989 A | 7/1999 | Polz |
| 5,951,484 A | 9/1999 | Hoium et al. |
| 5,954,664 A | 9/1999 | Seegobin |
| 5,957,856 A | 9/1999 | Weil et al. |
| 5,957,861 A | 9/1999 | Combs et al. |
| 5,961,467 A | 10/1999 | Shimazu et al. |
| 5,974,341 A | 10/1999 | Er et al. |
| 5,978,707 A | 11/1999 | Krig et al. |
| 6,004,020 A | 12/1999 | Bartur |
| 6,004,276 A | 12/1999 | Wright et al. |
| 6,007,493 A | 12/1999 | Ericksen et al. |
| 6,014,581 A | 1/2000 | Whayne et al. |
| 6,016,442 A | 1/2000 | Hsu et al. |
| 6,016,447 A | 1/2000 | Juran et al. |
| 6,016,448 A | 1/2000 | Busacker et al. |
| 6,017,307 A | 1/2000 | Raines |
| 6,031,984 A | 2/2000 | Walser |
| 6,035,233 A | 3/2000 | Schroeppel et al. |
| 6,045,513 A | 4/2000 | Stone et al. |
| 6,073,049 A | 6/2000 | Alt et al. |
| 6,088,618 A | 7/2000 | Kerver |
| 6,091,990 A | 7/2000 | Hsu et al. |
| 6,101,415 A | 8/2000 | Er et al. |
| 6,101,416 A | 8/2000 | Sloman |
| 6,151,524 A | 11/2000 | Krig et al. |
| 6,240,317 B1 | 5/2001 | Villaseca et al. |
| 6,253,102 B1 | 6/2001 | Hsu et al. |
| 6,289,244 B1 | 9/2001 | Conley et al. |
| 6,289,248 B1 * | 9/2001 | Conley et al. .................. 607/59 |
| 6,301,503 B1 | 10/2001 | Hsu et al. |
| 6,308,100 B1 | 10/2001 | Er et al. |
| 6,308,102 B1 | 10/2001 | Sieracki et al. |
| 6,321,117 B1 | 11/2001 | Koshiol et al. |

| | | |
|---|---|---|
| 6,400,981 B1 | 6/2002 | Govari |
| 6,415,175 B1 | 7/2002 | Conley et al. |
| 6,418,340 B1 | 7/2002 | Conley et al. |
| 6,445,952 B1 | 9/2002 | Manrodt et al. |
| 6,449,504 B1 | 9/2002 | Conley et al. |
| 6,454,726 B1 | 9/2002 | Catt et al. |
| 6,690,972 B2 | 2/2004 | Colney et al. |
| 6,700,097 B1 | 3/2004 | Hsu et al. |
| 6,842,644 B2 | 1/2005 | Anderson et al. |
| 7,003,349 B1 | 2/2006 | Andersson et al. |
| 7,010,349 B2 | 3/2006 | Conley et al. |
| 7,089,056 B2 | 8/2006 | Koshiol et al. |
| 7,089,221 B2 | 8/2006 | Fromherz et al. |
| 7,117,163 B1 * | 10/2006 | Iyer et al. ............... 705/7.32 |
| 7,191,006 B2 | 3/2007 | Hu et al. |
| 7,613,672 B2 | 11/2009 | West et al. |
| 7,979,378 B2 | 7/2011 | West et al. |
| 2002/0049481 A1 | 4/2002 | Conley et al. |
| 2002/0156389 A1 | 10/2002 | Kalgren et al. |
| 2003/0125776 A1 | 7/2003 | Turney et al. |
| 2004/0111131 A1 | 6/2004 | Hu et al. |
| 2004/0116982 A1 | 6/2004 | Conley et al. |
| 2005/0010258 A1 * | 1/2005 | Peterson et al. ............ 607/32 |
| 2005/0010388 A1 | 1/2005 | Bagchi et al. |
| 2005/0033385 A1 | 2/2005 | Peterson et al. |
| 2005/0060198 A1 | 3/2005 | Bayne |
| 2006/0241822 A1 | 10/2006 | Yadappanavar et al. |
| 2006/0288046 A1 | 12/2006 | Gupta |
| 2008/0126968 A1 | 5/2008 | West et al. |
| 2010/0016996 A1 | 1/2010 | West et al. |

FOREIGN PATENT DOCUMENTS

| | | |
|---|---|---|
| WO | WO-9927992 A1 | 6/1999 |
| WO | WO-2007127596 A1 | 11/2007 |

OTHER PUBLICATIONS

"U.S. Appl. No. 11/380,570, Notice of Allowance mailed Jun. 24, 2009", 11 pgs.

"U.S. Appl. No. 11/380,570, Response filed Mar. 29, 2009 to Non Final Office Action mailed Dec. 22, 2008", 22 pgs.

"U.S. Appl. No. 12/566,212, Non-Final Office Action mailed Oct. 8, 2010", 13 pgs.

"U.S. Appl. No. 12/566,212, Notice of Allowance mailed Mar. 8, 2011", 11 pgs.

"U.S. Appl. No. 12/566,212, Response filed Jan. 10, 2011 to Non Final Office Action mailed Oct. 8, 2010", 13 pgs.

"International Application Serial. No. PCT/US2007/066237, International Search Report mailed Oct. 4, 2007", 3 pgs.

"International Application Serial No. PCT/US2007/066237, Written Opinion mailed Oct. 4, 2007", 5 pgs.

Sakkout, H. E., et al., "Probe Backtrack Search for Minimal Perturbation in Dynamic Scheduling", Kluwer Academic Publishers vol. 5, (2000), 359-388.

Wielinga, B., et al., "Configuration-Design Problem Solving", IEEE, (1997), 49-56.

US 7,010,348, 03/2006, Koshiol et al. (withdrawn)

* cited by examiner

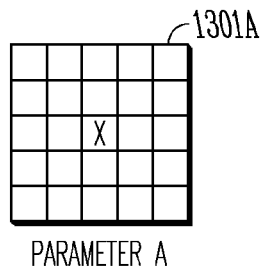

PARAMETER A

NORMALIZED WEIGHTS ARE SHOWN IN PARENS "(n)" (NORMALIZATION VALUE = 1/25 = 0.04)

| CHOICE #12A W=78 (3.12) | CHOICE #7A W=28 (1.12) | CHOICE #2A W=3 (.12) | CHOICE #3B W=6 (.24) | CHOICE #8B W=36 (1.44) |
|---|---|---|---|---|
| CHOICE #11A W=66 (2.64) | CHOICE #6A W=21 (.84) | CHOICE #1A W=1 (.04) | CHOICE #4B W=10 (.40) | CHOICE #9B W=45 (1.80) |
| CHOICE #10A W=55 (2.20) | CHOICE #5A W=15 (.60) | STARTING POINT W=0 (0) | CHOICE #5B W=15 (.60) | CHOICE #10B W=55 (2.20) |
| CHOICE #9A W=45 (1.80) | CHOICE #4A W=10 (.40) | CHOICE #1B W=1 (.04) | CHOICE #6B W=21 (.84) | CHOICE #11B W=66 (2.64) |
| CHOICE #8A W=36 (1.44) | CHOICE #3A W=6 (.24) | CHOICE #2A W=3 (.12) | CHOICE #7B W=28 (1.12) | CHOICE #12B W=78 (3.12) |

*FIG. 13A*

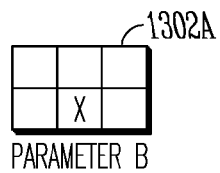

PARAMETER B

NORMALIZED WEIGHTS ARE SHOWN IN PARENS "(n)" (NORMALIZATION VALUE = 1/6 = 0.17 APPROX.)

| CHOICE #3A W=6 (1.02) | CHOICE #1A W=1 (.17) | CHOICE #1B W=1 (.17) |
|---|---|---|
| CHOICE #2A W=3 (.51) | STARTING POINT W=0 (0) | CHOICE #2B W=3 (.51) |

*FIG. 13B*

POSSIBLE SETTINGS OF PARAMETER A AND PARAMETER B
(SHOWING PARENTS AND CHILDREN)

SYSTEMS AND METHODS FOR AUTOMATICALLY RESOLVING INTERACTION BETWEEN PROGRAMMABLE PARAMETERS

CLAIM OF PRIORITY

This application is a continuation of U.S. application Ser. No. 12/566,212, filed Sep. 24, 2009, now issued as U.S. Pat. No. 7,979,378, which is a continuation of U.S. application Ser. No. 11/380,570, filed Apr. 27, 2006, now issued as U.S. Pat. No. 7,613,672, which are hereby incorporated by reference in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2003, Cardiac Pacemakers Inc., All Rights Reserved.

TECHNICAL FIELD

This document relates generally to medical systems, devices, and methods, and particularly, but not by way of limitation, to cardiac rhythm management systems and methods for constraint-illustrative parameter entry.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems often include a cardiac rhythm management device that is implanted in the patient to deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which typically synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The shock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart. Cardiac rhythm management systems often include external local or remote user interfaces (sometimes referred to as "programmers" or "patient management systems") for programming parameters (constraints) of an implantable cardiac rhythm management device or receiving data telemetered from the implantable cardiac rhythm management device.

One problem faced by cardiac rhythm management systems and other Personal Programmable Medical Devices ("PPMD") is in using an external user interface to program its parameters, such as to tailor the therapy delivered to the needs of the particular subject being treated by that device. For example, programmable implantable cardiac rhythm management devices often make use of a plethora of programmable parameters. Moreover, such programmable parameters may interact with each other. For example, programming a first parameter to a particular value may limit the range of particular values to which a second parameter may be programmed. Because of this interaction between different programmable parameters, a complex set of constraints typically governs how the set of parameters may be programmed. Consequently, a physician faces a daunting task in programming the whole set of parameters to self-consistent values. Moreover, as new therapies are developed (e.g., congestive heart failure therapies that treat both left and right sides of the heart), more parameters and more interactions between parameters are inevitable, further complicating the task of programming a complete set of parameters to allowable values. In addition, new implantable, programmable medical device systems for applications other than the heart itself are continuously developed, ever increasing the number of potential parameters and interactions between parameters. Often, programming one parameter or a set of parameters to a particular value results in invalid results when combined with other interdependent parameter values, causing a complex trial and error analysis for the user. One method of reducing the difficulty of programming parameter values is through establishing manufacturer's default values. This method, however, does not allow the flexibility needed by the physician to specifically tailor a treatment to a particular patient.

Tailoring treatment for a particular patient typically requires programming one or more parameters of the device away from the manufacturer's default values. The current method used to program a PPMD is very inefficient when a large number of parameter interdependencies exist. Often, complex parameter interaction constraints govern interdependencies between parameters. Such parameter interaction constraints are typically defined by the PPMD manufacturer.

To program one or more parameters away from the manufacturer defaults, a user-specified set of parameter values is obtained from the user, and automatically compared to the parameter interaction constraints to determine whether a constraint violation has occurred. If no constraint violation exists, the user-specified parameters are accepted into the PPMD. However, if a constraint violation does exist, the user may be advised of one or more of the violation's existence, the reason for the violation, or a description of the nature of the constraint rule. However, it is then typically left entirely up to the user to modify the existing set of parameter values to try to remove the violation without inadvertently triggering another violation. In fact, this can be a complex and daunting task.

While it may sometimes be possible for the user to achieve a violation-free second set of parameters in a short number of iterations and an acceptable amount of time, the existence of more parameters will typically increase the number of iterations needed and the difficulty of achieving any acceptable set of violation-free parameter values. This decreases the productivity of the user (in most cases a physician), and increases the possibility of errors.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 13A, 13B, 13C, and 13D illustrate an example of the interaction resolution engine ordering candidate second sets of parameter values.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present inventors have recognized a need for improved techniques for assisting a physician, caregiver, or other user in programming parameter values by automatically determining, from a user-specified input set of parameter values, if possible, a second set of parameter values for a PPMD such as an implantable cardiac rhythm management device. This document discusses, among other things, systems, devices, and methods that will be described in applications involving implantable or external Personal Programmable Medical Devices (PPMDs). Examples of PPMDs include, among other things, implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
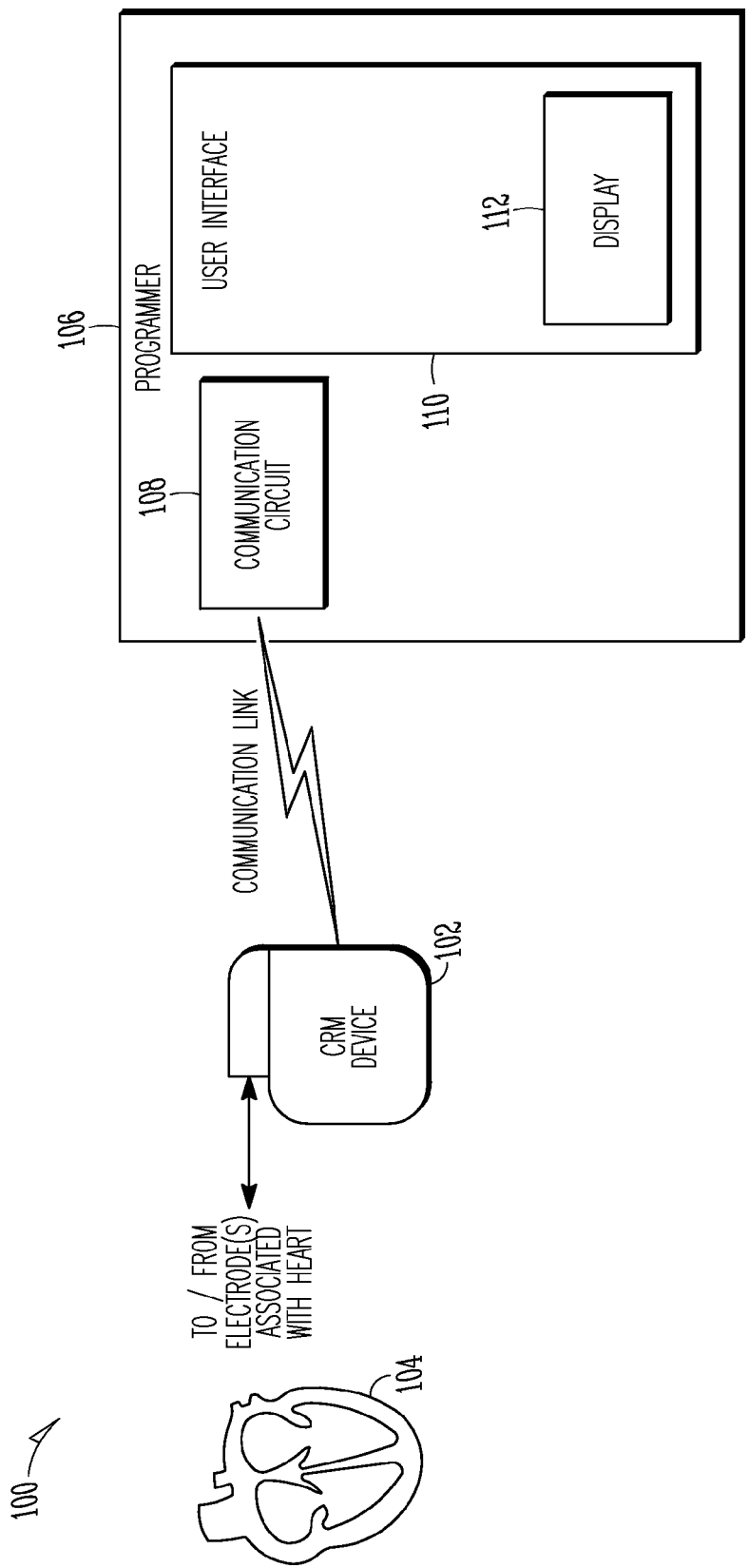
FIG. 1 is a schematic diagram illustrating generally, by way of example, but not by way of limitation, portions of a Programmable Personal Medical Device (PPMD) such as an implantable cardiac rhythm management system.

FIG. 1 is a block diagram illustrating generally portions of a cardiac rhythm management system 100 and portions of an environment in which it is used. In this example, system 100 includes a cardiac rhythm management device 102 coupled to a heart 104 by one or more electrodes associated with heart 104, such as for sensing intrinsic cardiac signals and/or for delivering energy or other therapy to heart 104. System 100 also includes a remote external programmer 106. Programmer 106 includes a telemetry or other communication circuit 108, which is wirelessly or otherwise communicatively coupled to a telemetry or other communication circuit in device 102. In a remote external programmer 106 example, sometimes referred to as an advanced patient management system, the communication link may include intermediary devices, such as a repeater, or one or more communications networks. Device 102 includes (by way of example, but not by way of limitation) a pacer, a defibrillator, a cardiac resynchronization therapy (CRT) device, a monitor, a device that combines more than one of these functions, or any other implantable or external device for diagnosing or treating medical conditions. The controller or processor typically also includes, or is coupled to, a memory circuit for storing data. In one example, device 102 is sized and shaped for being pectorally or abdominally implanted in a human patient. The electrode(s) coupling device 102 to heart 104 may include an intravascular electrode, an intracardiac electrode, an epicardial electrode, or a housing or a header electrode located on a housing of device 102 or a header attached thereto, or any combination of the above. In some configurations, such as where portion(s) of device 102 are external to the patient, the electrode(s) coupling device 102 to heart 104 may include a skin surface electrode external to the patient. The electrodes may be associated with the heart for bipolar (i.e., two electrodes that are relatively close together) or for unipolar (i.e., two electrodes that are farther apart) signal sensing or therapy energy delivery (e.g., pacing pulse or shocks).

In the illustrative example of FIG. 1, programmer 106 includes a controller or processor that is capable of sequencing through various control states such as, for example, by using a digital microprocessor having executable instructions stored in an associated instruction memory circuit, a microsequencer, or a state machine for storing data. Programmer 106 also includes a user input/output interface 110, which includes a display 112. Among other things, a physician or other caregiver (or, in certain cases, the patient) uses user interface 110 for programming therapy and other operative parameters of device 102. As discussed above, such parameters are often subject to a complex set of constraints governing how they interact with each other. This often makes the task of programming a consistent set of values for the various interdependent parameters extremely difficult for the user. Moreover, because some of these parameters are used for tailoring the particulars of therapy being delivered to the subject, the programming of appropriate values for these parameters is often very important to providing proper therapy to the subject. In addition, as new implantable or external PPMDs are developed for various applications, this often tends to increase the number of potential parameters and interactions between parameters. Often, programming a particular parameter value yields invalid results when combined with other interdependent parameter values, subjecting the user to a complex trial and error process when programming the PPMD. For these and other reasons, the present inventors have recognized a need for improved techniques for assisting a physician, caregiver, or other user in programming parameter values, such as by automatically determining, if possible, a second set of parameter values for an implantable, PPMD such as an implantable cardiac rhythm management device.

Figure 2:
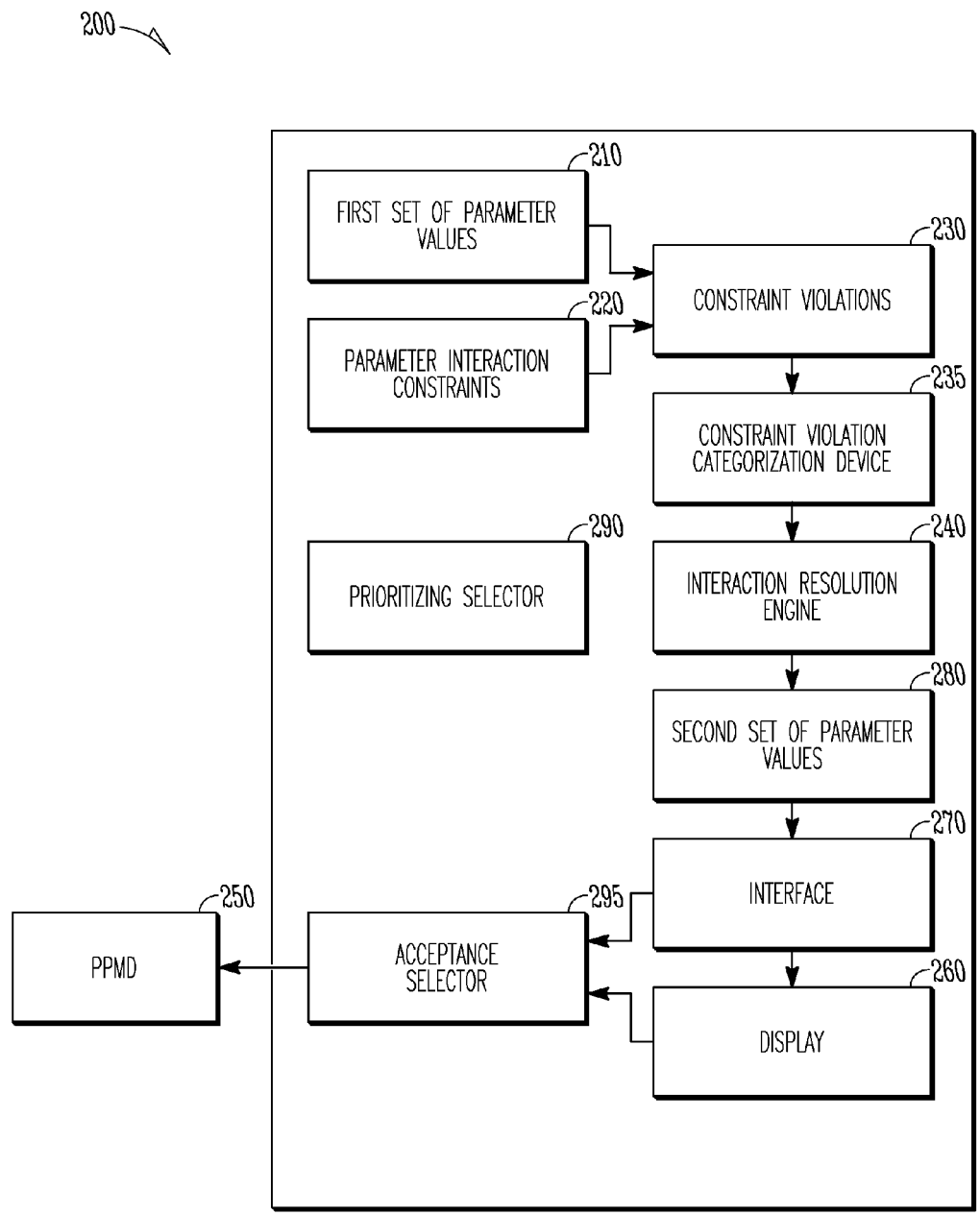
FIG. 2 illustrates a block diagram of a system including a PPMD and an interaction resolution engine.

FIG. 2 illustrates a block diagram of portions of system 200 for programming a multi-parameter PPMD 250. In this example the system 200 includes a display 260 and an interface 270 for communicating with a user. In this example, a first set of parameter values 210 typically includes user-specified desired values of parameters for the PPMD 250. Parameter interaction constraints 220 create one or more interdependencies between different programmable parameters. These constraints will restrict which values are acceptable for the user-specified first set of parameter values 210. The user specified first set of parameter values 210 is automatically checked against such constraints 220 to ensure that the user-specified set of parameter values 210 are acceptable before they are programmed into the PPMD 250. The PPMD manufacturer typically defines such restrictions, such as based on safe operating conditions for the PPMD 250.

The automatic comparison of the first set of parameter values 210 to the parameter interaction constraints 220 may result in a first set of one or more constraint violations 230. In certain examples, a constraint violation categorization module 235 categorizes a particular constraint violation, such as by severity into two or more categories (e.g., "unacceptable", "undesirable but acceptable", etc.). In certain examples, a constraint violation that would result in the PPMD functioning incorrectly is typically categorized as a "warning," while a constraint violation that may result in unconventional—but permissible—prescription is typically categorized as an "attention."

In the example of FIG. 2, if one or more constraint violations 230 exist, then an interaction resolution engine 240 attempts to automatically determine a suitable second set of proposed parameter values 280 while: (1) avoiding or reducing the degree or number of constraint violations; and (2) reducing or minimizing an indication of a variation between the first and second sets of parameter values. In certain examples, a prioritizing selector 290 permits the user to select one or more parameters to be given a higher priority with respect to whether it should be held static or constant. If an acceptable second set of parameter values 280 is found, an acceptance selector 295 is presented to the user. The user can then accept or reject the proposed second set of parameter values. If accepted, the user may then program the second set of parameter values into the PPMD 250. If rejected, the user is allowed to specify another first set of parameter values, which, if not violation-free, can be used as another user-specified starting point for another attempt to automatically find an acceptable second set of parameter values.

If no facially acceptable second set of parameter values 280 can be automatically determined by the interaction resolution engine 240, then the user is notified that no acceptable second set of parameter values could be found.

Figure 3:
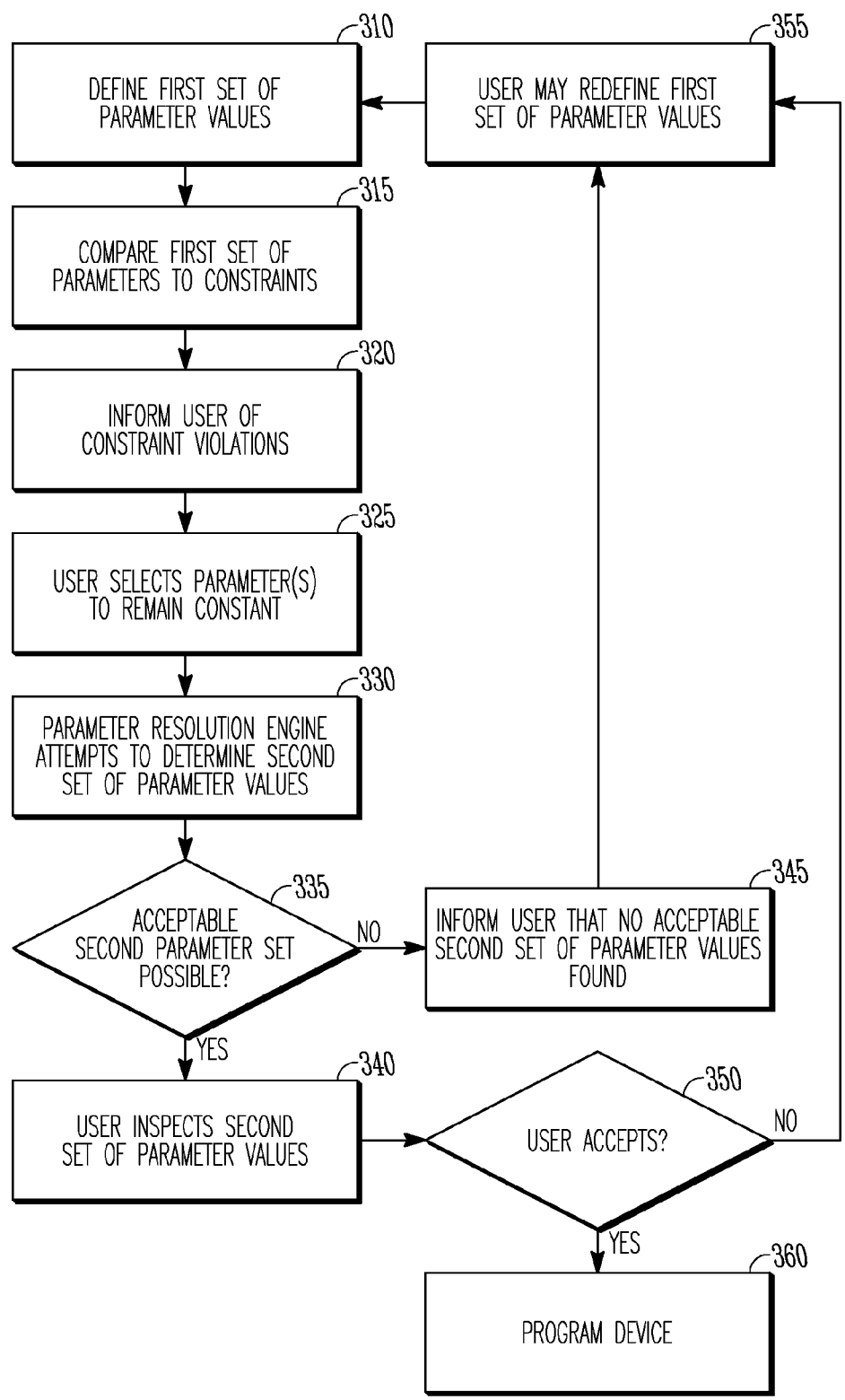
FIG. 3 illustrates a flowchart diagram of an example of a method of programming a PPMD.

FIG. 3 illustrates a flowchart diagram of an example of a method of programming a PPMD. At 310, a first set of parameter values is determined. The first set of parameter values is typically user-specified, or supplied by user input. However, the first set of parameter values could also be determined automatically, such as based on measurements from one or more PPMD. In one example, these measurements are device measurements, such as lead impedance of the PPMD, or the remaining battery power in the PPMD. In another example, these measurements are measurements of patient characteristics, such as thoracic fluid status, or a measurement of the patients state of activity. In any case, the first set of parameter values is capable of taking on values other than the manufacturer-specified default parameter values, since such manufacturer-specified default values would presumably be violation-free and, therefore, would not have any need for the present techniques of resolving or reducing such violations.

At 315, the first set of parameter values 210 is compared to the parameter interaction constraints 220. A first set of parameter interaction constraint violations (if any) is created by comparing the first set of parameter values 210 to the parameter interaction constraints 220. At 320, in this example, the user is informed of the constraint violations 230. The message at 320 may also include one or more explanations about the constraint violations, such as a textual or graphical explanation of the underlying rule being violated. If one or more constraint violations 230 exist, then at 325 the user can either manually remedy the constraint violation, or alternatively request that the constraint violation be automatically remedied. In certain examples, to request automatic remediation of the constraint violation, the user uses the prioritizing selector 290 to select one or more parameters from the parameters associated with the first set of parameter values 210 that the user wants held constant in value during the automatic violation remediation. At 325, the interaction resolution engine 240, holding constant the one or more parameters specified by the user, attempts to automatically determine a second set of parameter values 280, while holding various parameter values as close as possible to the first set of parameter values. At 335, if the interaction resolution engine is able to automatically determine an acceptable second set of parameter values, then at 340 the second set of parameter values is displayed to the user for approval. At 350, the user reviews the second set of parameter values 280. If the user approves the automatically-generated second set of parameter values 280, then at 360 the user may then program the PPMD with the second set of parameter values 280. If the user does not approve of the second set of parameter values 280, then at 355 the user may redefine the first set of parameter values 210, and may again request automatic determination of an acceptable set of parameter values, such as based on the redefined first set of parameter values 210.

At 335, if the interaction resolution engine 240 is unable to find an acceptable second set of parameter values 280, then the user is informed that no acceptable solution could be found. The message may also explain why no solution could be found. At 335 the user may redefine the first set of parameter values 210, and may again request automatic determination of an acceptable set of parameter values, such as based on the redefined first set of parameter values 210.

The method of FIG. 3 provides a significant advantage over current methods of programming a PPMD. The method of FIG. 3 may reduce the number of iterations needed to determine a suitable second set of parameter values, while maintaining the user's ability to inspect and accept or reject a particular set of automatically computed values. This increases the user's efficiency of programming a PPMD. Such time savings provide opportunity for cost savings as well.

Figure 4:
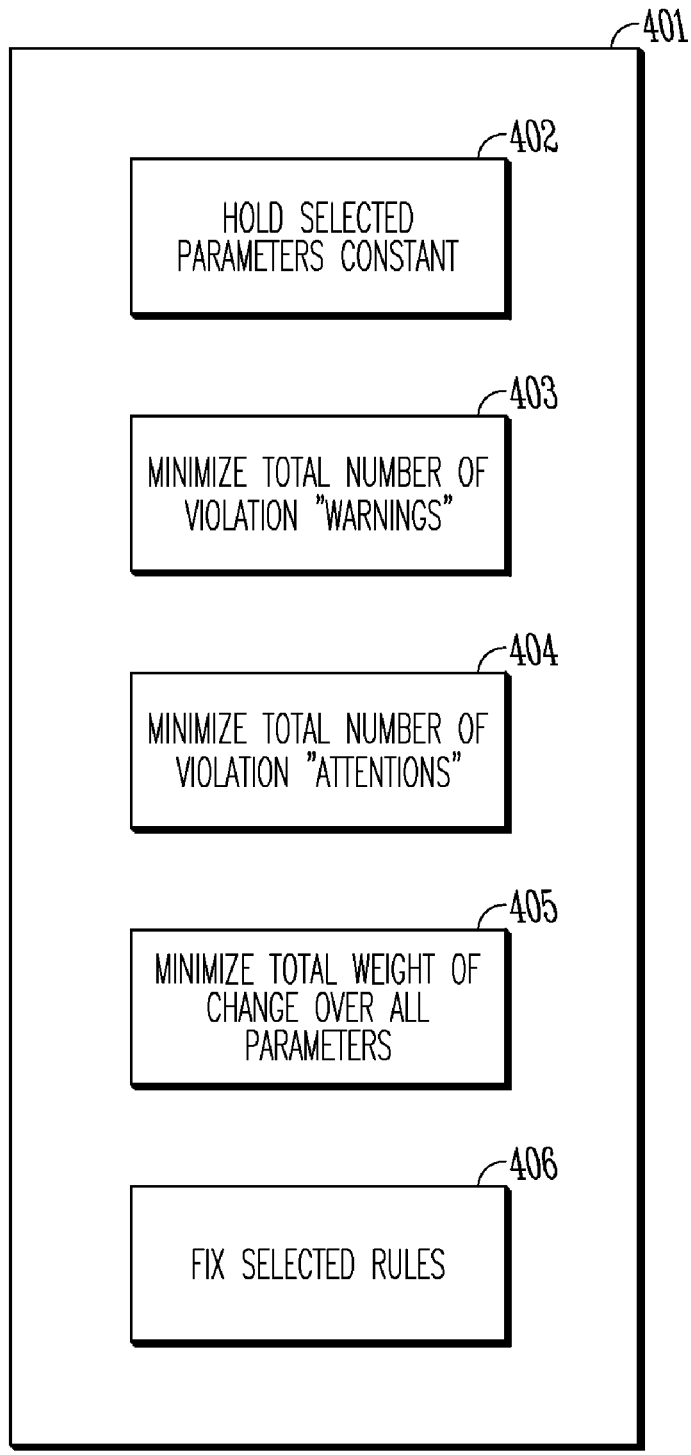
FIG. 4 illustrates an example of certain goals of the interaction resolution engine.

FIG. 4 illustrates an example of certain goals of the interaction resolution engine 401. In certain examples, at 402, the interaction resolution engine 401 holds one or more user-selected parameters constant. In certain examples, at 403, the interaction resolution engine 401 attempts to minimize the total number of violation "warnings." In certain examples, at 404, the interaction resolution engine 401 attempts to minimize the total number of violation "attentions." In certain examples, at 405, the interaction resolution engine 401 attempts to minimize a total weight of change over all parameters in the parameters set. This assumes that the user-specified initial starting point values (e.g., the first set of parameter values) were highly desired. Therefore, in automatically determining a new set of parameter values to address any constraint violations, one goal is to minimize deviation from the first set of parameter values. In certain examples, at 406, the interaction resolution engine 401 attempts to fix selected one or more rules specified by the user, or all rules for which a violation exists.

Figure 5:
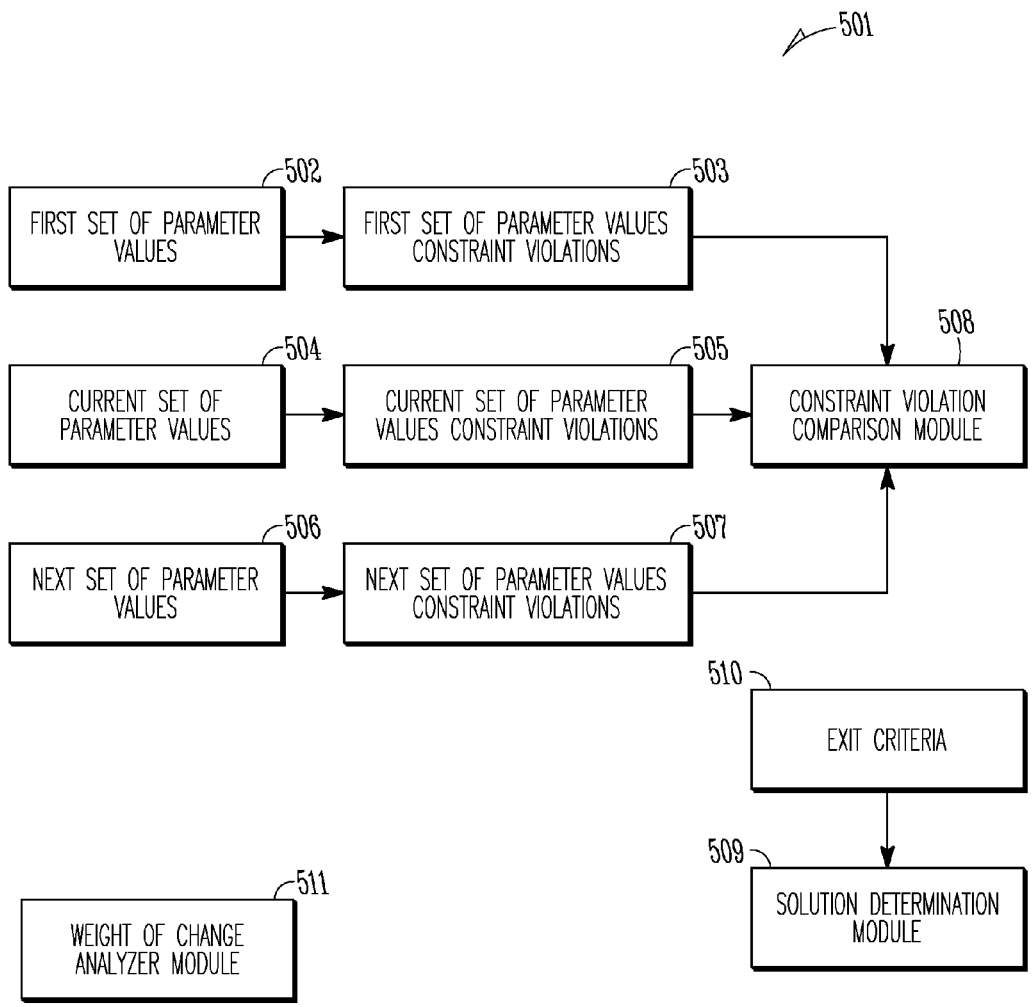
FIG. 5 illustrates a block diagram of an example of the interaction resolution engine.

FIG. 5 illustrates a block diagram example 501 of portions of the interaction resolution engine 240 and its environment. In this example, a first set of parameter values 502 is user-specified. Constraint violations 503 arise when the first set of parameter values 502 is automatically checked against one or more constraints. A parameter constraint violation comparison module 508 compares constraint violations between various parameter sets to determine which parameter set is associated with less egregious constraint violations.

In one example, a particular set of parameter values is deemed to include less egregious violations than another set of parameter values if fewer "warnings" are associated with the particular set of parameter values.

In another example, a particular set of parameter values is deemed to include less egregious violations than another set of parameter values if both sets of parameter values include an equal number of associated "warnings," but fewer "attentions" are associated with the particular set of parameter values.

During the automatic parameter value determination process, the current set of parameter values 504 is a placeholder (e.g., for best known parameter values so far) that may change in value during the course of the automatic parameter determination analysis performed by the interaction resolution engine 240. The current set of parameter values 504 holds the then-current set of parameter values with less egregious constraint violations compared with all other sets of parameter values so far analyzed by the interaction resolution engine 240. The current set of constraint violations 505 are the one or more constraint violations (if any) associated with the then-current set of parameter values 504.

During the automatic parameter value determination process, a next set of parameter values 506 is a placeholder that changes in value during the course of the automatic interaction resolution engine analysis. The next set of parameter values 506 includes a potential second set of parameter values. A next set of constraint violations 507 are the one or more constraint violations 230 (if any) associated with a next set of parameter values 506. In certain examples, the solution determination module 509 organizes candidate second parameter sets according to a computed relative weight of change with respect to the first set of parameter values.

One or more exit criteria 510 determine when the interaction resolution engine 240 should complete its automatic parameter interaction resolution analysis. In one example, the interaction resolution engine 240 exits upon automatically finding a set of parameter values with no associated constraint violations ("attentions", "warnings"). In another example, the interaction resolution engine 240 exits upon reaching a defined maximum number of tests of various combinations of parameter values. In one example, the interaction resolution engine 240 exits upon exhausting all possible combinations of parameter values. In certain examples, a solution determination module 509 determines whether a solution has been found. In certain examples, a weight of change analyzer 511 determines an order in which potential second sets of parameter values become considered as the next parameter set 507. The weight of change analyzer 511 may order the potential second parameter sets so that those sets of potential second parameter values that are closest in value to the first set of parameter values 502 are considered before potential second parameter sets that are further in value from the first set of parameter values 502.

Figure 6:
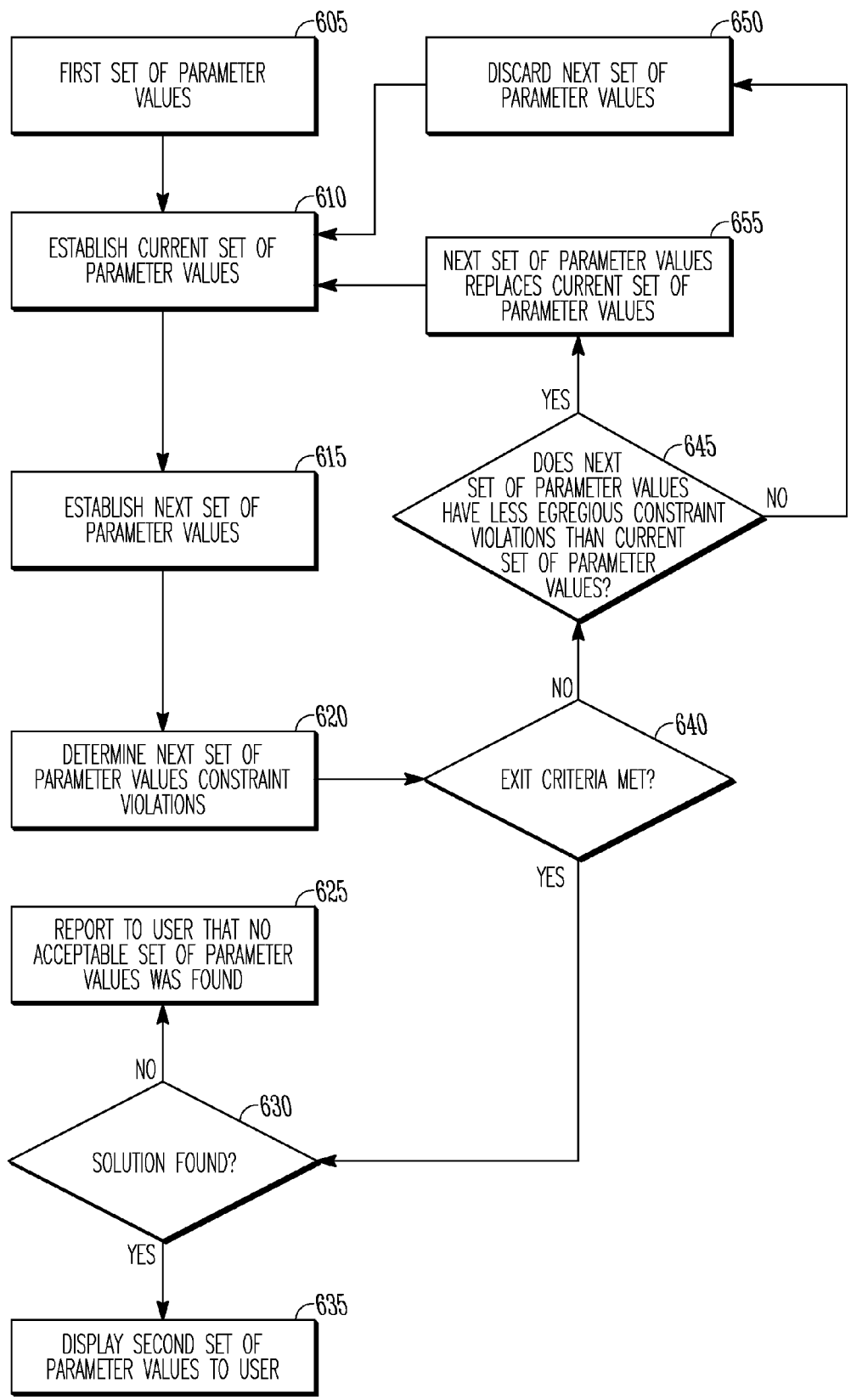
FIG. 6 illustrates generally a flow chart diagram of an example of how the interaction resolution engine determines second set of parameter values, if possible.

FIG. 6 illustrates generally a flow chart diagram of an example of how the interaction resolution engine 240 determines a second set of parameter values 280, if possible. At 605, a first set of parameter values 502 is obtained. At 610, a current set of parameter values is obtained. Initially, at 610, the current set of parameter values is seeded as equal to the first set of parameter values. At 615, a next set of parameter values is established. One example of a method used to determine ordering of potential second sets of parameter values is described below with respect to FIG. 7. At 620, the next set of parameter values is compared to the parameter interaction constraints 220 to determine what, if any, next set of parameter values constraint violations 507 exist.

At 640, the interaction resolution engine 240 determines whether any exit criteria 510 are satisfied. If so, then at 630 the solution determination device 509 determines whether a solution has been found. At 635, if the current set of parameter values 504 is different than the first set of parameter values 502 supplied by the user, the solution determination module 509 provides the current parameter set to the user as the proposed second parameter set. In one example, the interaction resolution engine 240 may also require that original constraint violation, which prompted the user to select a parameter to remain constant, be resolved before providing a second parameter set to the user. At 625, if the current set of parameter values 504 is identical to the first set of parameter values 502 supplied by the user, then no solution has been found, in which case, at 625 a message is displayed to the user explaining that no solution could be found.

If, at 640, no exit criteria are met, then at 645 the current set of parameter values' constraint violations 505 are compared to the next set of parameter values' constraint violations calculated at 620. If the current set of parameter values' constraint violations 505 are less egregious or equal to the next set of parameter values' constraint violations 507, then at 650 the next set of parameter values is discarded. At 610, the current set of parameter values is maintained with no change in value, and at 615 a new next set of parameter values is obtained.

If, at 645, the current set of parameter values' constraint violations 505 are less egregious than the next set of parameter values' constraint violations 507, then at 610 the next set of parameter values replaces the current set of parameter values 655. At 615, a new next set of parameter values is established. The method illustrated in FIG. 6 continues until, at 640, one or more exit criteria 510 are met.

In certain examples, the interaction resolution engine 240 uses the weight of change analyzer to determine the order of potential/candidate second parameter sets by the weight of change compared to the first set parameter values. Analyzing a set of parameter values with a lesser weight of change from the first set of parameter values 502 before those with a greater weight of change from the first set of parameter values may be advantageous, as opposed to an analysis where the next set of parameter values are computed randomly or by some other method. The weight of change analysis can be used to ensure that if two sets of parameter values are associated with equally egregious constraint violations, that set of parameter values with the least weight of change value, compared to the first set of parameter values, becomes the resultant second set of parameter values 280. Using the weight of change method to order the candidate sets of parameter values for consideration also may reduce the number of computational iterations needed to find a second set of parameter values 280. The weight of change analysis can also be used to ensure that if a second set of parameter values is found with no constraint violations, satisfying exit criteria 510, the second set of parameter values is the closest violation-free set of parameter values to the first set of parameter values 502. In certain examples, the weight of change of all potential sets of parameter values is calculated, and stored in an array, each array element ordered by the weight of change from the first set of parameter values 502. The array can be used to select each successive next set of parameter values in correspondence with the sequence of the elements in the array.

Figure 7A:
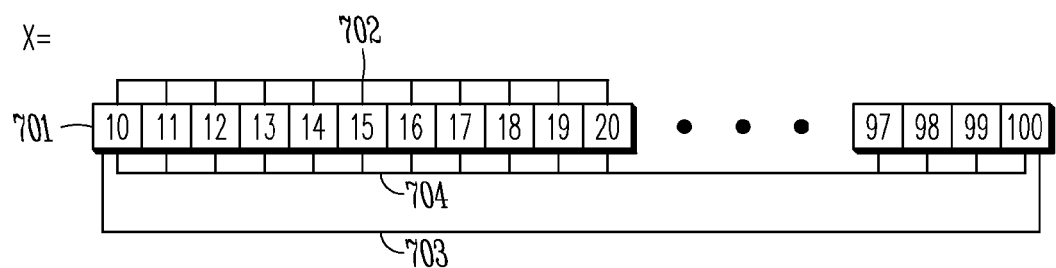
FIG. 7a illustrates an example of candidate values of a parameter X.

FIG. 7A illustrates an example of potential values of a particular parameter X. In this example, the candidate values of X are held in an array. In this example, candidate values of X 701 have a range of values 703 from 10 to 100. In this example, the candidate values of X can be any integer value within the range of values 703. In this example, there are 91 candidate values, or total number of 90 steps 704 (i.e., 91−1=90 steps) between candidate values, for parameter X. The difference between any two candidate values can be characterized by a number of steps 702 between candidate values. In this example, the number of steps between a candidate value of 10 and a candidate value of 20 is 10 steps.

Figure 7B:
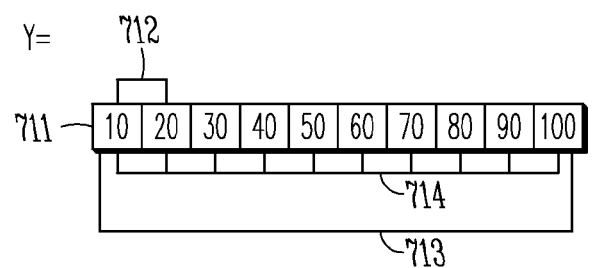
FIG. 7b illustrates an example of candidate values of a parameter Y.

FIG. 7B illustrates an example of candidate values of a particular parameter Y. In this example, the candidate values of Y are held in an array. In this example, candidate values of Y 711 have a range of values 713 from 10 to 100. In this example, the permissible candidate values of Y can be any multiple of 10 within the range of values 713, such as 10, 20, 30, 40, etc. Thus, in this example, there are 10 total candidate values, or total number of 9 steps 714 between candidate values (i.e., 10−1=9 steps) for parameter Y. The difference between any two candidate values can be characterized as a number of steps 712 between such candidate values. In this example, for parameter Y, the number of steps between a candidate value of 10 and a candidate value of 20 is one step.

Figure 8:
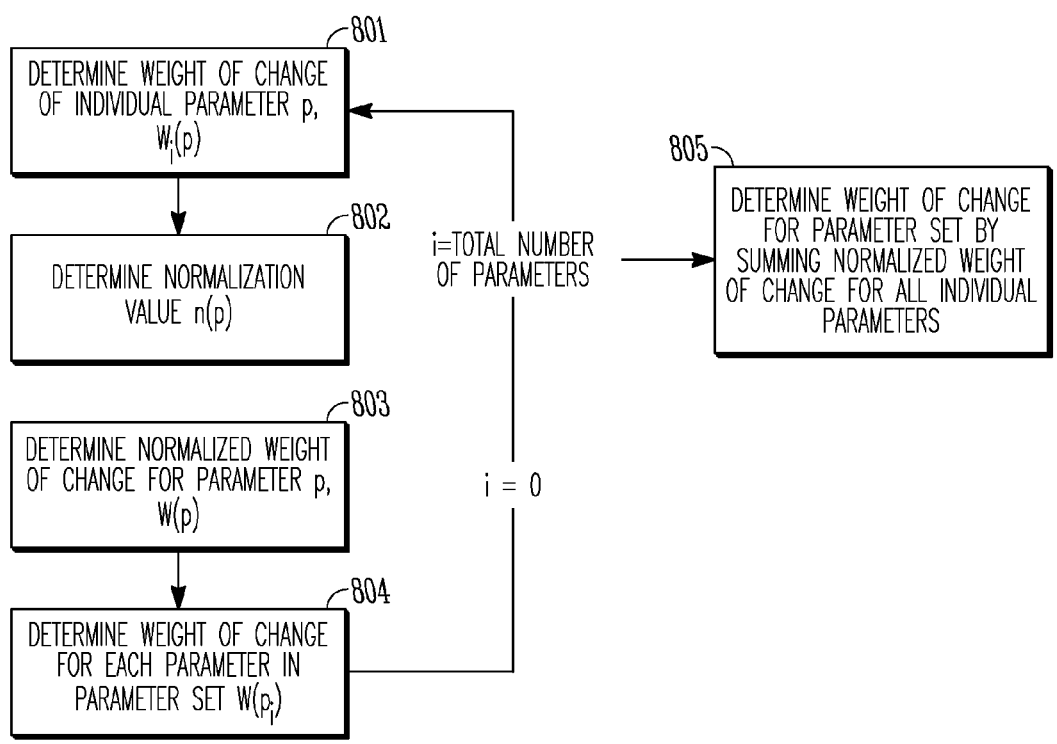
FIG. 8 illustrates a simplified example of one method of determining the weight of change for a set of parameter values.

FIG. 8 illustrates a block diagram of one method of determining a weight of change for a set of parameter values. First, at 801, the weight of change of a particular parameter value $W_v(p)$ is determined. As illustrated in FIG. 7a and FIG. 7b, the number of steps between values 702 or 712, or s(p), describes the difference between two values for of a particular parameter p. $W_v(p)$ is based on the number of steps between the value of parameter p in the first set of parameter values and the value of p in the second set of parameter values.

$W_v(p) = [(s(p))^2 + s(p)]/2$ where s(p) = the number of steps from parameter p's value in the initial set of parameter values.

As an illustrative example, assume that the value of both parameters X and Y in the first set of parameter values is 50. In the example of FIG. 7A, assume that the value of parameter X in the second set of parameter values is 80. For the example of FIG. 7A, this yields a difference of 80−50=30 intervening values, or steps between the value of parameter X in the first set of parameter values and parameter X in the second set of parameter value. Accordingly, s(X) is equal to 30.

In the example of FIG. 7B, assume that the value of parameter Y in the second set of parameter values is also 80. Because the example of FIG. 7B has a difference of 3 possible values (or 3 steps), between the value of parameter Y=50 in the first set of parameter values and parameter Y=80 in the second set of parameter value, s(Y) is equal to 3.

Using the $((s(p))^2 + s(p))$ function helps maintain values close to the starting point. Its result, $W_v(p)$, increases exponentially with the number of steps away from a starting point value. Such a weighting ensures that potential next set of parameter values 506 are ordered by how close they are in value to the first set of parameter values 502.

For the example of FIG. 7A, because the value of s(X) is 30, the value of $W_v(X)$ is equal to $((30^2) + (30))/2$, or 465. For the example of FIG. 7b, because the value of s(Y) is equal to 3, the value of $W_v(Y)$ is equal to 6.

At 802, a normalization value n(p) is determined using only one of either: (a) the total number of steps 704 or 714 for a particular parameter p, or (b) the total number of candidate values for the particular parameter p. Where normalizing by the total number of steps, for the example of FIG. 7a the normalization value n(X), or the total number of steps 704, is equal to 90 because there are 91 candidate values for parameter X. For the example of FIG. 7b the total number of steps 714, or n(Y) is equal to 9, because there are 10 possible values for parameter Y. Alternatively, the normalization could be by the total number of candidate values, such that n(X)=91 for parameter X of FIG. 7A and n(Y)=10, for parameter Y of FIG. 7B. For a case where there is a single candidate value for a parameter (i.e., not multiple candidate values), it may be advantageous to normalize by the total number of candidate values rather than the total number of steps, to avoid any division by zero during the normalization process.

At 803, a normalized weight of change for a parameter p, W(p), is determined. W(p) is equal to the weight value, $W_v(p)$ of a parameter p, divided by the normalization value n(p) of the parameter p.

n(p) = total number of candidate values for parameter p
W(p) = $W_v(p)$/n(p)

In the above equation, the normalization divides by the total number of candidate values for parameter p, rather than by the alternative of dividing by the total number of steps for the candidate p.

In the example of FIG. 7A, the value of $W_v(X)$ is 465. The corresponding value of n(X) is 91. Therefore, the resulting value W(p)=465÷91=5.11. In the example of FIG. 7B, the corresponding value of $W_v(Y)$ is 6. The value of n(X) is 10. Therefore, the resulting value W(p)=6÷10=0.6. Contrast this example with using an analysis where no weight of change is taken into account. The example of FIG. 7A (30 steps), would be considered much further away than the example of FIG. 7B (3 steps), by a factor of 10 (ratio of 30 to 3). Instead, using the weight of change analysis, these values only differ by a factor of about 8.5 (ratio of 5.11 to 0.6). Thus, using the weight of change analysis results in a movement of one step being attributed a greater weight when there are fewer candidate values to choose from.

At 804, this method is applied to each parameter in the set of parameter values. At 805, when a weight of change $W(p_i)$ has been determined for each parameter in the set of parameter values, a total weight of change $W_t$ for the entire set of parameter values is determined by summing the individual weight of change $W(p_i)$ of each parameter in the set of parameter values.

FIGS. 13A, 13B, 13C, and 13D illustrate an example of how the interaction resolution engine 240 may order candidate second sets of parameter values by weight of change. In this example, there are three parameters in the first set of parameter values 502: A, B, and C. The values of the parameters result in a constraint violation. In this example, the user has selected parameter C to remain constant.

Figure 13C:
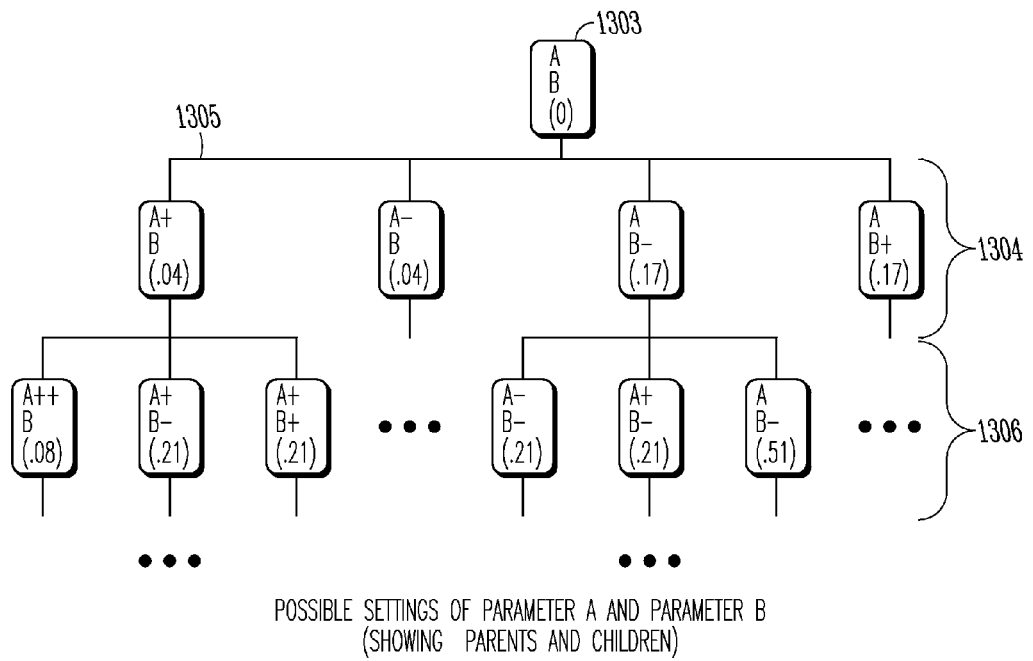

FIG. 13A depicts a Parameter A, having 25 candidate values that are arranged, in this example, in a thumbnail two-dimensional Table 1301A, which is blown up into a larger two-dimensional Table 1301B, to illustrate further details. Similarly, FIG. 13B depicts a Parameter B, having six candidate values that are arranged, in this example, in a thumbnail two-dimensional Table 1302A, which is blown up into a larger two-dimensional Table 1302B. In each of the thumbnail Tables 1301A and 1302A, an "x" depicts a starting point value, which is selected from the starting point value set 1303, as shown in FIG. 13C.

The two-dimensional nature of the Tables 1301A-B and 1302A-B is not required. For example, the candidate values of Parameter A could be conceptualized as extending linearly from the starting point in two directions. In such an arrangement, a first direction would include choices #1a, #2a, #3a, #4a, #5a, #6a, #7a, #8a, #9a, #10a, #11a, and #12a. The second direction would include choices #1b, #2b, #3b, #4b, #5b, #6b, #7b, #8b, #9b, #10b, #11b, and #12b. Similarly, the candidate values of Parameter B could be conceptualized as extending linearly from the starting point in two directions. In such an arrangement, a first direction would include choices #1a, #2a, and #3a. The second direction would include choices #1b, and #2b.

In each box of Tables 1301B and 1302B, the non-normalized weight is indicated (e.g., W=1 for choice #1a in Table 1301B), along with a parenthetical indicating the corresponding normalized weight value (e.g., 0.4 for choice #1a in Table 1301B).

Figure 13D:
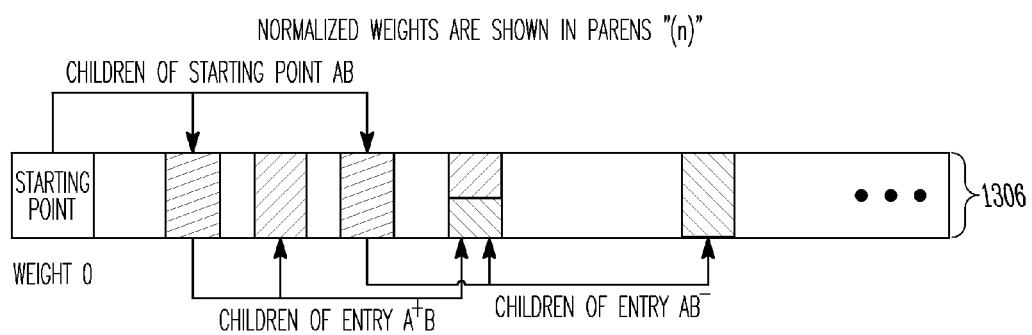

FIG. 13C illustrates an example of a tree or candidate value combinations that is generated by the interaction resolution engine 240, and FIG. 13D illustrates an example of a linear array into which candidate value combinations are placed, in an order that is determined using the normalized weight of change. In this example, the starting point value set 1303 is the original user-specified combination or set of parameter values. In this example, the interaction resolution engine 240 determines the children 1304 of the starting point value set 1303. Such children 1304 are those combinations of parameters A and B that are one step away from the starting point value set 1303. For example, in the children 1304, the child $A^+B$ represents choice #1b in Table 1301B in combination with the starting point in Table 1302B. The child $A^-B$ represents choice #1a in Table 1301B in combination with the starting point in Table 1302B. The child $AB^-$ represents the starting point in Table 1301B in combination with the choice #1a in Table 1302B. The child $AB^+$ represents the starting point in Table 1301B in combination with the choice #1b in Table 1302B. Each of these children 1304 is one step away from the starting point value set 1303, and these children 1304 are ordered in the tree of FIG. 13C in a manner such that the child having the smallest normalized weight of change occupies the left-most position in the tree, and the child having the largest normalized weight of change occupies the right-most position in the tree.

In certain examples, after the children 1304 are determined by the interaction resolution engine 240, they are inserted into a linear Weighted Possible Setting Array 1308 of FIG. 13D, which is ordered according to the normalized weight of change. In this example, the Weighted Possible Setting Array 1308 includes the starting point (zero normalized weight of change) at its left-most position, with normalized weight of change increasing in a rightward direction from this starting point.

Because the combinations $A^+B$ and $A^-B$ have smaller normalized weights of change than the combinations $AB^-$ and $AB^+$, the former are placed to the left of the latter in the array 1308. To select the next set of parameter values 506 for comparison to the current set of parameter values 504, as described previously with respect to FIGS. 5 and 6, combinations are extracted from the weighted possible setting array 1308 from left to right, that is, from the smaller normalized weights of change to larger normalized weights of change.

In this example, this means that the combination $A^+B$ is established as the next set of parameter values at 615 of FIG. 6. If no exit criteria are found at 640, then the children 1306 of $A^+B$ are determined and placed in the ordered array 1308. Then, the next left-most combination (here, $A^-B$) is established as the next set of parameter values 615 of FIG. 6. If no exit criteria are found at 640, then the children 1306 of $A^-B$ (not shown in FIG. 13C) are determined and placed in the ordered array 1308. Then, the next left-most combination, here, $A^{++}B$, is established as the next set of parameter values 615 of FIG. 6. This process continues until either an exit criteria is met, or no further combinations from Tables 1301B and 1302B are available in the linear array 1308 to be used as the next set of parameter values at 615.

Figure 9:
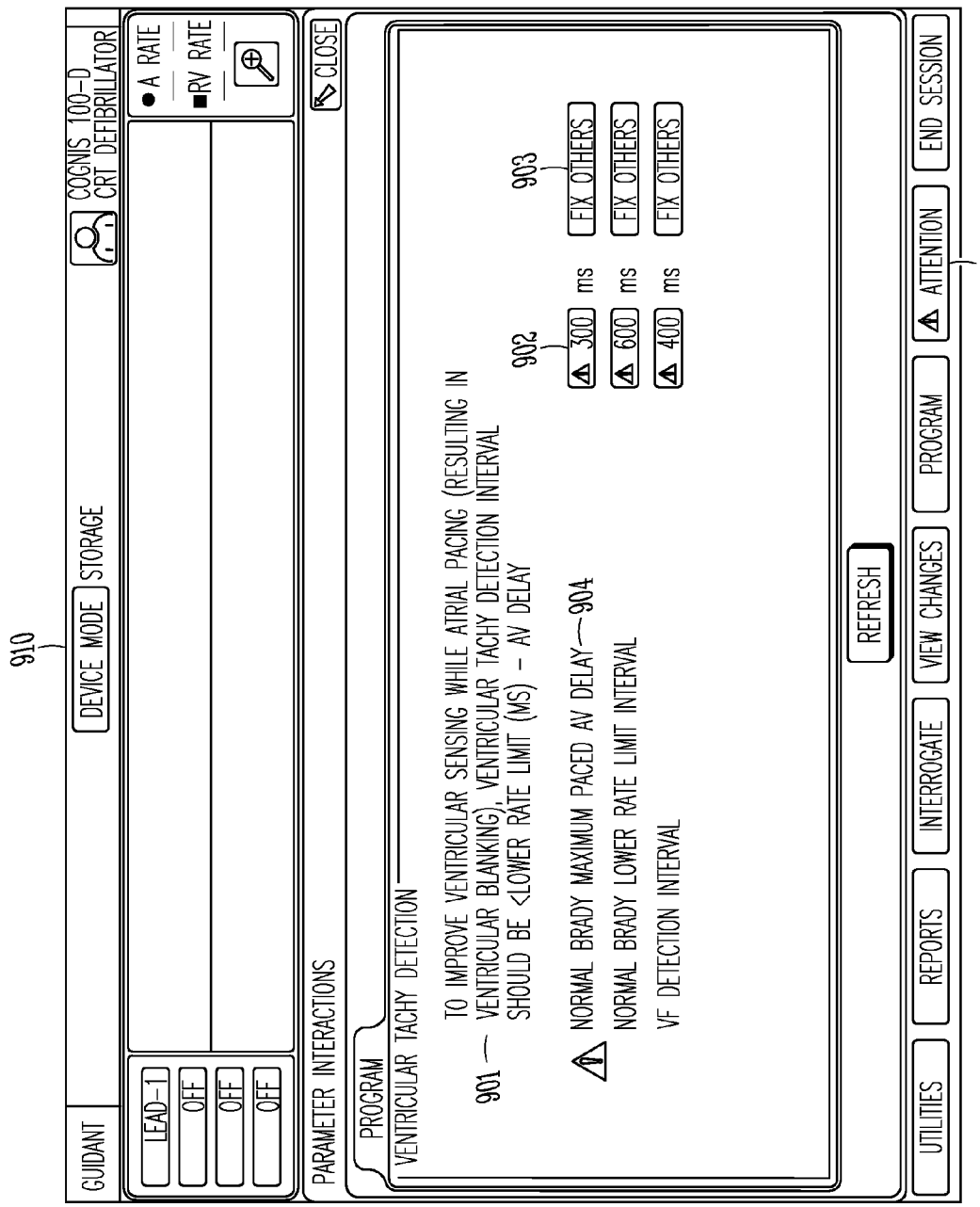
FIG. 9 illustrates an example of a screen shot of the display communicating an "attention" to the user.

FIG. 9 illustrates an example of a screen shot 910 of the display 260 communicating a "attention" 905 to the user of the PPMD. In this example, the display 260 shows a textual description of the violated constraint 901. In addition, the display 260 shows the particular parameters on which the constraint violation depends 904, and the values of those parameters 902. In this example, each listed parameter includes a "Fix Others" button 903 that can be selected by the user to hold that particular parameter constant at its then-existing value while automatically resolving constraints.

Figure 10:
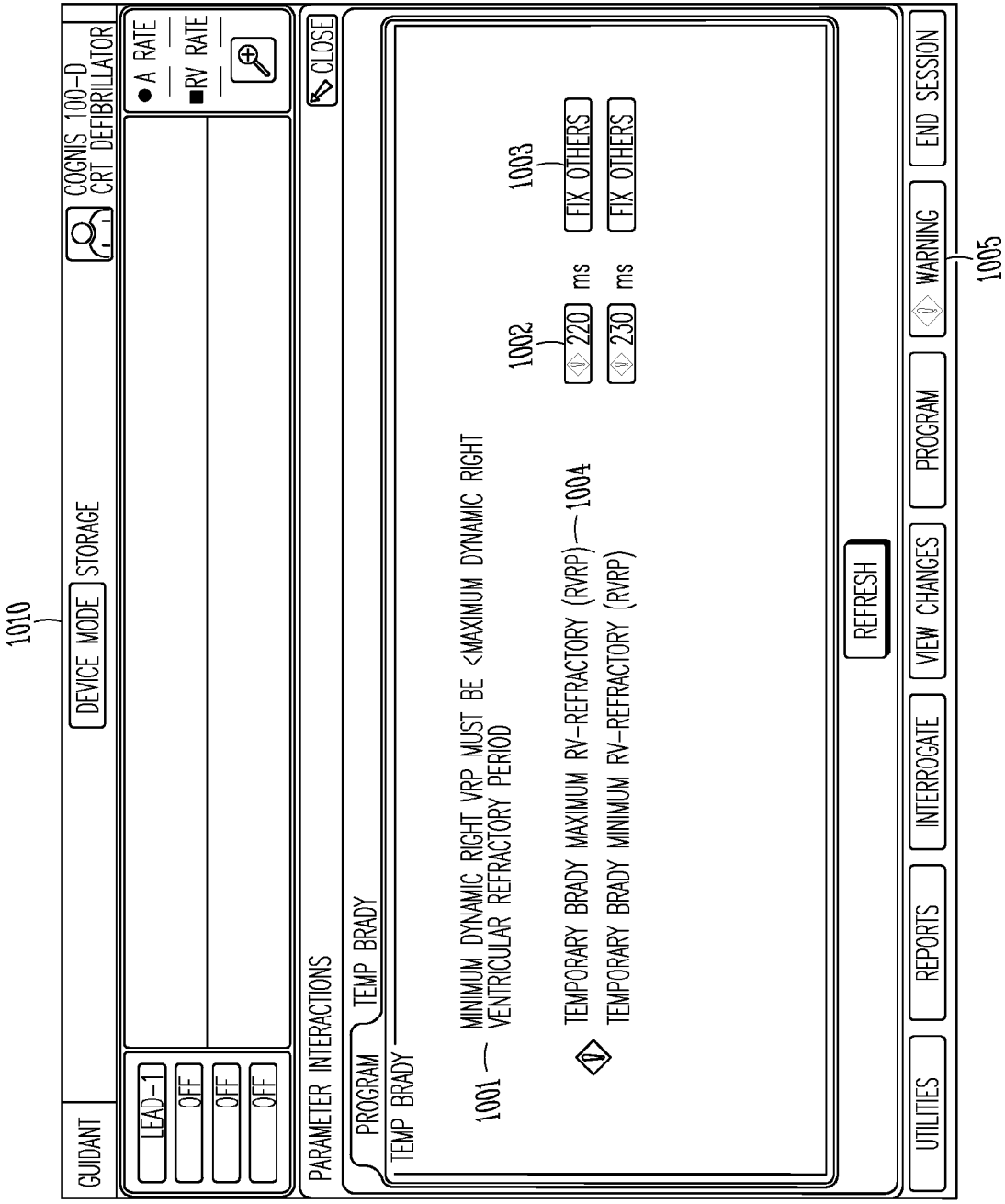
FIG. 10 illustrates an example of a screen shot of the display communicating a "warning" to the user.

FIG. 10 illustrates an example of a screen shot 1010 of the display 260 communicating a "warning" 1005 to the user of the PPMD In this example, the display 260 shows a textual description of the violated constraint 1001. In addition, the display 260 shows the particular parameters on which the constraint violation depends 1004, and the values of those parameters 1002. In this example, each listed parameter includes a "Fix Others" button 1003 that can be selected by the user to hold that particular parameter constant at its then-existing value while automatically resolving constraints.

Figure 11:
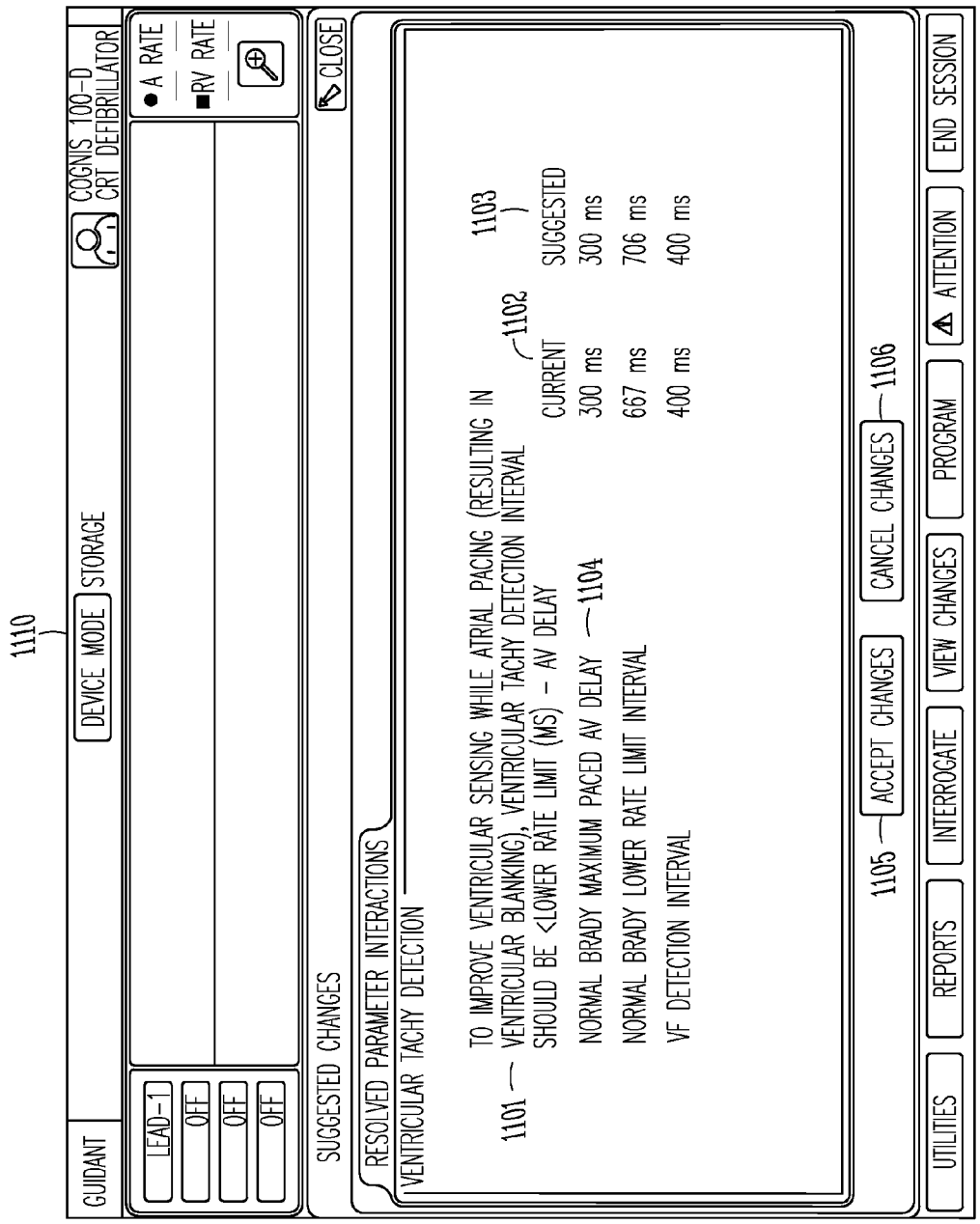
FIG. 11 illustrates an example of a screen shot of the display communicating a second set of parameter values to the user.

FIG. 11 illustrates an example of a screen shot 1110 of the display 260 communicating a second set of parameter values to the user. In this example, the display shows the first set of parameter values 1102, the constraints violated by the first set of parameter values 1104, and an explanation of the constraints violated by the first set of parameter values 1101. In addition, the display shows a second set of parameter values 1103. The user is given the opportunity to accept 1105 or reject 1106 the acceptable set of parameter values 1103.

Figure 12:
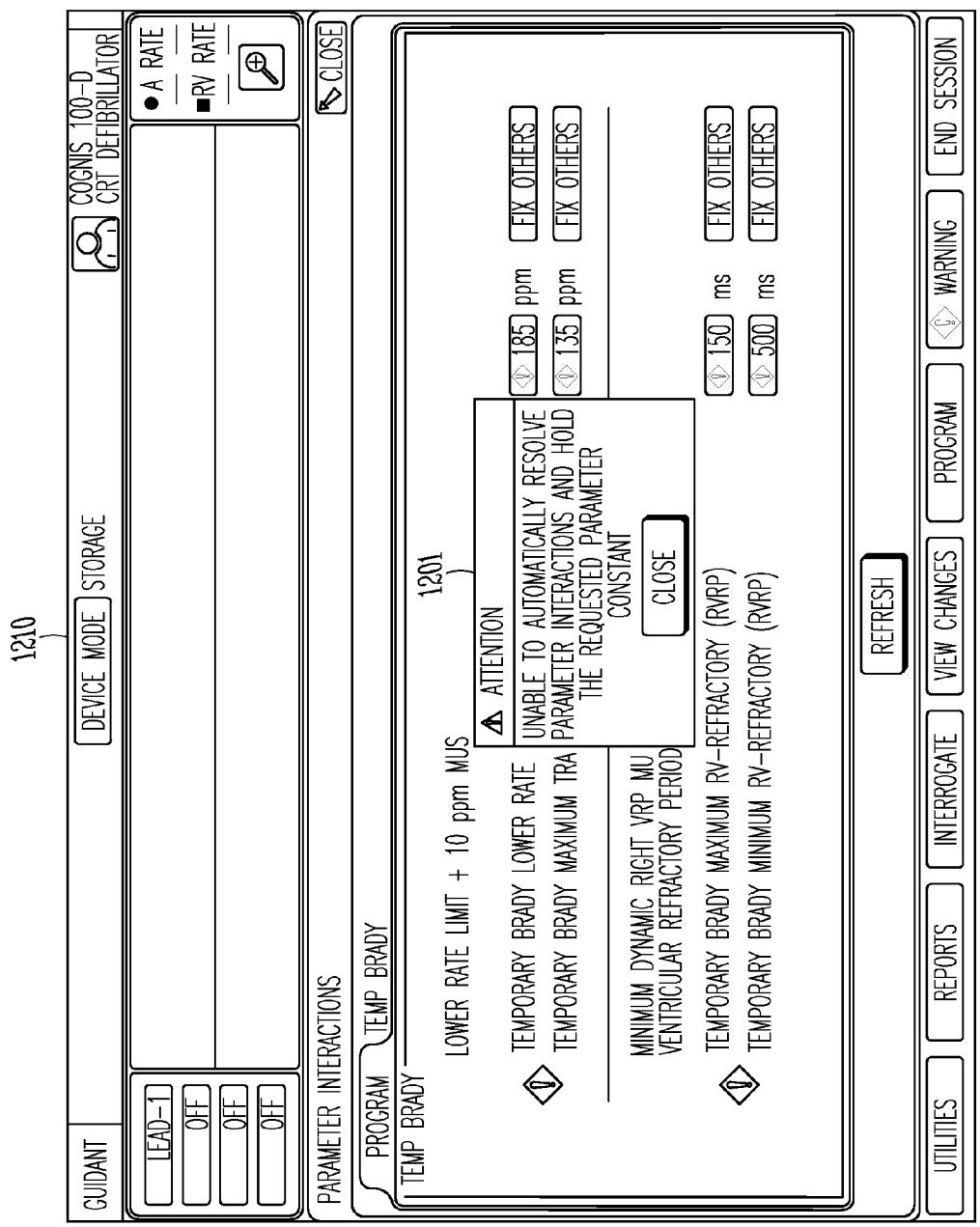
FIG. 12 illustrates an example of a screen shot communicating to the user that the parameter interaction resolution engine was unable to resolve parameter interactions.

FIG. 12 illustrates an example of a screen shot 1210 communicating to the user 1201 that no second set of parameter values could be found.

Operation of the interaction resolution engine 240 is not limited to the above examples. In another example, a user selects one or more particular constraint violations from a list, and is then presented with a list of parameters on which the one or more constraint violations depend. The user may then select one or more parameters to remain constant. In one example, a constraint violation exists, and the user is presented with all parameters for a given medical device. The user then selects one or more parameters from the list to remain constant.

In another example, the user is presented with a "Fix This One" or "Fix These Ones" button. The user selects one or more parameters that may be modified. In this example all non-selected parameters are held constant while the interaction resolution engine 240 attempts to determine a solution based on modification of the selected parameters.

In another example, a "Fix This Rule" button is presented to the user. In this example, the user selects one or more parameter interaction constraints with associated constraint violations. The interaction resolution engine 240 attempts to determine a solution based on modifying those parameters that affect the selected one or more parameter interaction constraints, while holding constant all parameters that do not affect the selected one or more constraints. In another example, a "Fix All Rules" button is presented to the user. In this example, the user need not select any particular parameter to be held constant; all parameters can be used in forming candidate combinations of parameter values for determining a possible solution.

In various examples, determining the most advantageous solution to resolve parameter violations is not limited to the above examples. In an example, as opposed to organizing candidate solution sets of parameter values by weight of change, the candidate set of parameter values are organized in any other suitable fashion. In another example, the candidate set of parameter values are organized by a specified ranking of their importance in desired operation of the medical device. In other examples, candidate solution set of parameter values are organized by other criteria.

In various examples, particular parameter values are precluded from user selection to remain constant. In various examples, particular parameter values are not included in the analysis of candidate acceptable set of parameter values. In various examples, set of parameter values with a limited number of candidate values, such as an on/off value, are not included in the analysis of potential acceptable set of parameter values. In an example, due to certain conditions, if it can be determined that modification of a first set of parameter values will not yield a second set of parameter values prior to analyzing that first set of parameter values, a user is notified that analysis is not possible.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system for programming a multi-parameter programmable personal medical device, the system comprising:
   a processor; and
   a memory device coupled to the processor, the memory including instructions that, when performed by the processor, cause the processor to:
   compare a first set of user-programmable parameter values against a plurality of interaction constraints to produce an indication of a first violation of at least one of the plurality of interaction constraints when the first violation of at least one of the plurality of interaction constraints exists;
   create a plurality of candidate sets of parameter values;
   determine a weight of change, with respect to the first set of parameter values, for each candidate set of parameter values;
   determine, from the first set of parameter values, a second set of parameter values that reduces the first violation and adjusts a plurality of parameters with respect to the first set of parameter values; and minimize the weight of change with respect to the first set of parameter values, in determining the second set of parameter values.

2. The system of claim 1, wherein the memory includes instructions that, when performed by the processor, cause the processor to:
determine the first set of user-programmable parameter values using a value received from the multi-parameter programmable personal medical device.

3. The system of claim 2, wherein the instructions that cause the processor to determine the first set of user-programmable parameter values include instructions to interpret the value received from the multi-parameter programmable personal medical device.

4. The system of claim 3, wherein the instructions to interpret the value received from the multi-parameter programmable personal medical device includes instructions to interpret the value of at least one of:
a lead impedance measurement;
a battery status reading; or
a patient characteristic.

5. The system of claim 1, wherein the memory includes instructions that, when performed by the processor, cause the processor to request redefinition of the first set of parameter values when the interaction resolution engine fails to present an acceptable second set of parameter values.

6. The system of claim 1, wherein the memory includes instructions that, when performed by the processor, cause the processor to:
accept a fixed parameter value for one of the parameters in the first set of user-programmed parameter values; and
determine the second set of parameter values while holding the fixed parameter value constant.

7. The system of claim 1, wherein the memory includes instructions that, when performed by the processor, cause the processor to determine the second set of parameter values using a specified maximum number of candidate sets of parameter values.

8. The system of claim 1, wherein the memory includes instructions that, when performed by the processor, cause the processor to determine a set of parameter values, of the plurality of candidate sets of parameter values, that includes no constraint violations.

9. The system of claim 1, wherein the memory includes instructions that, when performed by the processor, cause the processor to accept input indicating acceptance of the second set of parameter values for programming into the multi-parameter programmable personal medical device.

10. A method for programming a medical device, the method comprising:
comparing, using one or more processors, a first set of user-programmable parameter values against a plurality of interaction constraints to produce an indication of a first violation of at least one of the plurality of interaction constraints;
creating a plurality of candidate sets of parameter values;
determining a weight of change, with respect to the first set of parameter values, for each candidate set of parameter values;
determining, from the first set of parameter values using the one or more processors, a second set of parameter values that reduces the first violation and adjusts a plurality of parameters with respect to the first set of parameter values; and
minimizing, using the one or more processors, the weight of change with respect to the first set of parameter values, in determining the second set of parameter values.

11. The method of claim 10, further comprising determining the first set of user-programmable parameter values from a value received from the medical device.

12. The method of claim 11, wherein the determining the first set of user-programmable parameter values includes interpreting the value received from the medical device.

13. The method of claim 12, wherein the interpreting the value received from the medical device includes interpreting the value of at least one of:
a lead impedance measurement;
a battery power reading; or
a patient characteristic.

14. The method of claim 10, further comprising requesting redefinition of the first set of parameter values when an acceptable second set of parameter values cannot be determined.

15. The method of claim 10, further comprising:
accepting a fixed parameter value for one of the parameters in the first set of user-programmed parameter values; and
wherein determining the second set of parameter values includes holding the fixed parameter value constant.

16. The method of claim 10, further comprising receiving input indicating acceptance of the second set of parameter values for programming into the multi-parameter programmable personal medical device.

17. A machine-readable medium including instructions that, when performed by a processor, cause the processor to:
determine a first set of parameter values for programming a medical device based on a value received from the medical device;
compare the first set of parameter values against a plurality of interaction constraints to produce a first violation of one of the plurality of interaction constraints;
create a plurality of candidate sets of parameter values;
determine a weight of change, with respect to the first set of parameter values, for each candidate set of parameter values;
determine, from the first set of parameter values, a second set of parameter values that reduces the first violation and adjusts a plurality of parameters with respect to the first set of parameter values;
minimize, while creating the second set of parameter values, the weight of change, with respect to the first set of parameter values, of the second set of parameter values; and
program a medical device according to the second set of parameter values.

18. The machine-readable medium of claim 17, wherein the instructions that cause the processor to determine the first set of parameter values include instructions that further cause the processor to interpret the value received from the medical device while determining the first set of parameter values.

19. The method of claim 18, wherein the instructions that cause the processor to interpret the value received from the medical device include instructions that cause the processor to interpret the value of at least one of:
a lead impedance measurement;
a battery status reading; or
a patient characteristic.

* * * * *